(12) United States Patent
Taylor et al.

(10) Patent No.: US 8,845,747 B2
(45) Date of Patent: Sep. 30, 2014

(54) PROSTHESIS

(75) Inventors: Andrew Clive Taylor, Chichester (GB); Michael Anthony Tuke, Guildford (GB); Jonathan Robert Thomas Jeffers, Guildford (GB)

(73) Assignee: Finsbury (Development) Limited (GB)

( * ) Notice: Subject to any disclaimer, the term of this patent is extended or adjusted under 35 U.S.C. 154(b) by 119 days.

(21) Appl. No.: 13/378,593

(22) PCT Filed: Jun. 18, 2010

(86) PCT No.: PCT/GB2010/051013
§ 371 (c)(1),
(2), (4) Date: Feb. 22, 2012

(87) PCT Pub. No.: WO2010/146398
PCT Pub. Date: Dec. 23, 2010

(65) Prior Publication Data
US 2012/0150310 A1  Jun. 14, 2012

(30) Foreign Application Priority Data
Jun. 18, 2009  (GB) .................................. 0910552.9

(51) Int. Cl.
| | |
|---|---|
| *A61F 2/32* | (2006.01) |
| *A61F 2/34* | (2006.01) |
| *H05B 33/14* | (2006.01) |
| *H05B 33/10* | (2006.01) |
| *A61F 2/30* | (2006.01) |
| *A61F 2/46* | (2006.01) |
| *H01L 33/50* | (2010.01) |
| *A61F 2/00* | (2006.01) |

(52) U.S. Cl.
CPC ......... *A61F 2/34* (2013.01); *A61F 2002/30077* (2013.01); *A61F 2210/0066* (2013.01); *A61F 2002/30718* (2013.01); *A61F 2002/3446* (2013.01); *H05B 33/145* (2013.01); *A61F 2002/465* (2013.01); *H01L 33/508* (2013.01); *H05B 33/10* (2013.01); *A61F 2/0095* (2013.01); *A61F 2002/4681* (2013.01); *A61F 2002/3419* (2013.01); *H01L 33/501* (2013.01); *A61F 2/4609* (2013.01); *A61F 2310/00179* (2013.01); *A61F 2002/30561* (2013.01); *H01L 2933/0041* (2013.01)
USPC ..................................... 623/22.11; 623/22.12

(58) Field of Classification Search
CPC ..................................... A61F 2/32; A61F 2/34
USPC .......... 623/22.11, 22.12, 22.15, 22.19, 22.21, 623/22.34, 22.35, 22.43, 23.43, 23.56, 623/23.57, 22.23, 22.27, 22.31, 22.32, 623/22.37, 22.39; 606/91
See application file for complete search history.

(56) References Cited

U.S. PATENT DOCUMENTS 4,813,959 A * 3/1989 Cremascoli ................. 623/22.27
6,811,569 B1 * 11/2004 Afriat et al. ................. 623/22.32

(Continued)

FOREIGN PATENT DOCUMENTS

| | | |
|---|---|---|
| DE | 3533432 A1 | 9/1985 |
| EP | 743049 A1 | 11/1996 |

(Continued)

OTHER PUBLICATIONS

UK Search Report 0910552.9 date of search Jul. 5, 2010.

(Continued)

*Primary Examiner* — Thomas J Sweet
*Assistant Examiner* — Christopher D Prone (57) ABSTRACT

A cup prosthesis includes a cup, a band disposed about the outer circumference and adjacent to the rim of the cup, an impaction cap disposed at least partially within the space defined by the inner surface and the rim of the cup, and at least one flange extending from the band connected on one end to the impaction cap.

19 Claims, 14 Drawing Sheets

(56) References Cited

U.S. PATENT DOCUMENTS 7,597,715 B2 * 10/2009 Brown et al. ............ 623/22.32
2002/0177854 A1 * 11/2002 Tuke et al. ...................... 606/91

FOREIGN PATENT DOCUMENTS

| EP | 1666007 | A2 | 11/2005 |
|----|---------|----|---------|
| EP | 1634552 | A2 | 3/2006 |
| EP | 1721586 | A1 | 11/2006 |
| EP | 1592370 | B1 | 4/2008 |
| EP | 2008619 | A2 | 12/2008 |
| EP | 2008620 | A2 | 12/2008 |
| EP | 2174621 | A1 | 4/2010 |
| FR | 2789570 | A1 | 8/2000 |
| FR | 2909541 | A1 | 12/2006 |
| GB | 2323036 | A | 3/1997 |
| WO | WO 2006031911 | A2 | 3/2006 |
| WO | WO 2008103457 | A2 | 8/2008 |

OTHER PUBLICATIONS

PCT International Search Report and Written Opinion PCT/GB2010/051013 dated Sep. 15, 2010.

* cited by examiner

PROSTHESIS

CROSS REFERENCE TO RELATED APPLICATION

This application is a National Stage 35 U.S.C. 371 of International Patent Application PCT/GB2010/051013 filed Jun. 18, 2010.

BACKGROUND OF THE INVENTION

The present invention relates to a prosthesis. More particularly, it relates to a preassembled acetabular component.

The efficient functioning of the hip joint is extremely important to the well-being and mobility of the human body. Each hip joint is comprised by the upper portion of the femur which teiminates in an offset bony neck surmounted by a ball-headed portion which rotates within the acetabulum in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming misshapen.

Operations to replace the hip joint with an artificial implant are well-known and widely practiced. Generally, the hip prosthesis will be fottued of two components, namely: an acetabular component which lines the acetabulum; and a femoral component which replaces the femoral head. The femoral component may be total femoral head replacement in which case the component includes a head, neck and a stem which in use in inserted into the end of a prepared femur. Alternatively, where appropriate, the femoral head component may be a resurfacing prosthesis which is attached to the head of the femur once it has been suitably machined.

In an operation to insert a prosthetic acetabulum in a patient's pelvis the surgeon first uses a reamer to cut a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter with 2 mm increments between neighboring sizes.

There are a number of different types of prosthetic acetabular cups. One type of cup is made from polyethylene. They are generally cemented into the acetabulum and require only light pressure to seat them in the cement.

One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. However, in some arrangements, screws may be used to secure the cup shell in position in the pelvis before the liner is applied into position. The insertion of the metal shell into the pelvis requires considerable force. As the surgeon applies this force, there is a risk that the metal shell can become damaged or deformed. There is also a possibility that during the application of the force, the shell may move so that it is not in the optimum alignment in the acetabulum. Often the metal shells have outer surfaces or coatings which encourage bone to grow into them over time.

With this type of prosthesis, the polyethylene liner unit is snapped or screwed into the metal shell after the metal shell has been seated in the acetabulum. Thus the inner surface of the liner forms the socket part of the joint.

More recently, ceramics have been used as an alternative to the plastics liner. In this arrangement, the metal shell, which is generally formed from titanium and which is of a similar thickness to the arrangement in which a polyethylene liner is used, is inserted into the acetabulum. The ceramic liner is then inserted into the shell. It can be difficult for the liner to be accurately aligned in the shell. In addition, this insertion of the liner does require the application of a considerable force which is usually applied by the surgeon using a mallet often via an insertion tool. Considerable force is generally required to achieve a successful interface. However, this force can damage the ceramic liner.

In order to get an optimum fit, it is necessary that the forces applied for both the insertion of the metal shell and for the ceramic liner are appropriate but not excessive. One problem however, is that to date there has been no understanding as to what forces are appropriate nor is there a means to ensure that the correct force is applied.

The surgeon is not generally able to apply a controlled amount of force. Some surgeons may not apply sufficient force in one hit and it may be necessary for a plurality of hits to be used. These may not all strike at the same angle and may not each apply the same force. Other surgeons may apply a much greater single strike. The force applied by the surgeon on, for example, an insertion tool may vary considerably and can be of the order of about 3 to 5 kN but can also be much higher and may even be of the order of about 35 kN.

Whilst very large forces may only be applied for small moments in time, of the order of seconds or fractions of a second, forces of this magnitude, or a plurality of forces of smaller magnitude may cause the shell to be deformed as it is inserted into the acetabulum. This is a particular risk in those arrangements where the thickness of the shell is only from about 1 mm to about 3 mm. If the shell is deformed, it can become difficult or even impossible to insert the liner.

Additionally or alternatively, the liner may be incorrectly seated in the shell which can lead to various disadvantages. Not only is there a risk that where a portion of the liner stands above the rim of the cup, a point of irritation can be produced but also, there is a risk that material, such as wear debris, may congregate against the raised portion of the liner or against the wall of the cup in the area where the liner sits below the rim. This accumulation of debris may provide a site for post-operative infection. Even if the liner is correctly located and the shell is not deformed during the assembly process, it may become deformed on insertion of the prosthesis into the pelvis such that the shell may become spaced from the liner over at least a portion of the prosthesis.

Even if the surgeon is able to accurately seat the liner in the cup, there is a risk that during assembly debris may be caught between the liner and the cup which may affect the wear properties of the prosthesis. A further problem associated with the presence of debris, which may include fluids such as blood or fat, between the shell and liner is that in use, in vivo, the presence of the debris may cause the shell and liner to move apart.

Without wishing to be bound by any particular theory, it will be understood where the shell and ceramic liner are held together by friction, debris, in particular fatty substances or blood, can interfere with the frictional interface between the outer surface of the liner and the inner surface of the shell such that there is a propensity for the liner to move out of the shell.

A further problem which may be encountered is that while inserting the liner in the shell it may become damaged. If this damage is a chip or crack on the outer surface of the liner, i.e. on the surface adjacent to the surface of the shell, its presence may not be noticed by the surgeon during assembly. However, its existence will be a point of weakness which can result in the prosthesis failing in use.

One solution that has been proposed is to provide a preassembled unit of an acetabular cup prosthesis comprising: an outer shell; and a ceramic liner located within the shell. In one arrangement, the preassembled unit may be assembled ex-vivo under a controlled force selected to optimise the pre-stressing of the components of the prosthesis.

This arrangement provides an acetabular prosthesis which reduces the risk of liner misplacement and which has an enhanced life expectancy arising, in part, through improved resistance to damage caused during impaction into the acetabulum. The preassembled system also provides an acetabular cup prosthesis which can be easily handled and inserted during surgery without damage to the acetabular cup prosthesis and which minimizes the risk of debris being trapped between the cup and the liner.

Examples of such preassembled acetabular cup can be found in EP 7008619 and FP 7008620. Whilst the arrangements described therein address the aforementioned problems, there is a need for alternative arrangements.

In certain arrangements it may be desirable to provide an acetabular cup prosthesis which is made substantially from ceramic.

Whilst acetabular cup prostheses formed from ceramic offer various advantages, they may suffer from various disadvantages. The ceramic may not have sufficient strength to withstand the rigors of insertion. Further even if the ceramic cup can be successfully inserted in the pelvis without damage, due to the structure of the surface, there may be little or no torsional stability.

Even if the acetabular cup does include a thin metal shell, there may be a need to provide additional strength or additional torsional stability.

With a view to addressing this problem it has been proposed to provide an acetabular cup prosthesis comprising an acetabular cup having a rim and comprising a metal band applied around the outer circumference of the acetabular cup prosthesis and adjacent to said rim.

The presence of the metal band applied around the outer circumference of the acetabular cup prosthesis and adjacent the rim thereof provides additional strength to the prosthesis and in particular provides the required level of hoop compression.

This arrangement is discussed in EP 2174621 the contents of which are incorporated herein in their entirety.

To allow acetabular cups to be inserted in the pelvis, they may be connected to an impaction cap. The impaction cap may be pre-assembled with the prosthesis. Any suitable configuration of impaction cap may be used. One example of an impaction cap is described in EP 2008618 which is incorporated herein by reference.

It is desirable to provide suitable means for securing the impaction cap to the prosthesis particularly where the acetabular cup prosthesis is formed from ceramic and in particular where it has the arrangement described in EP 2174621.

BRIEF SUMMARY OF THE INVENTION

According to the present invention there is provided an acetabular cup prosthesis having a rim and comprising a metal band applied around the outer circumference of the acetabular cup prosthesis and adjacent to said rim, said cup prosthesis additionally comprising one or more flanges extending from the metal band and being configured such that in use the or each flange connects the prosthesis to an impaction cup.

The flanges are preferably frangible such that, once the prosthesis has been impacted into the acetabulum, they can be removed from the band such that they, and the impaction cap, can be removed.

The acetabular cup of the present invention may be formed of any suitable material. In a preferred embodiment the suitable material will be a ceramic. The term "ceramic" should be construed as meaning not only true ceramic materials but also other materials which display ceramic-like properties. Ceramic-like properties for the purposes of the present invention are those where the strength, stiffness and rigidity properties are similar to those of ceramics. Examples of suitable materials include glasses. In one arrangement a metal shell may be provided.

As discussed in EP 2174621, the prosthesis described therein has improved properties over prior art prosthesis. In particular, the described prosthesis has improved resistance to fracture. In particular where the cup is a ceramic cup or includes a ceramic liner, the presence of the band will serve to pre-stress the ceramic. This pre-stressing occurs during the controlled assembly process. Unstressed ceramic liners such as those of the prior art, are prone to fracture in use.

The band of the prosthesis is preferably made from metal. Whatever material the band is made from, the flanges will preferably formed from metal although plastics materials may also be used. Any suitable metal may be used, with titanium being particularly preferred. Cobalt/chromium may also be used.

The outer surface of the band may be provided with one or more ribs extending away from the cup. In use these ribs will interact with the pelvis to provide the required torsional stability. In one arrangement one or more, preferably three, ribs may be located at a plurality of points around the circumference of the band. In one arrangement one or more, preferably three ribs, may be located at equally spaced positions, preferably three equally spaced postions, around the circumference.

The ribs may be of any suitable configuration. Where there is more than one rib present, the ribs may be of the same or different configurations. In one arrangement, the, or each, rib may be a longitudinal extension.

In one arrangement, the band may be configured on its out surface to promote bone integration. In one arrangement, the outer surface may be coated with a bone growth promoting material such as hydroxyapatite.

In the embodiment where a shell is used, this may be coated on its outer surface with material to promote bone integration. In one arrangement, the outer surface may be coated with a bone growth promoting material such as hydroxyapatite.

Although not preferred, where a shell is used it may be a titanium shell. If used, the titanium shell has a thickness in the region of about 1 mm to about 3 mm.

The ceramic cup or liner may be formed of any material which has acceptable biocompatibility, hardness and wear resistance. Suitable ceramic materials include silicon nitride, doped silicon nitride, an alumina-zirconia ceramic, yttria, stabilized zirconia, ceria, stabilized zirconia, zirconia ceramics, alumina ceramics, oxinium or mixtures thereof The thickness of the ceramic cup or liner is preferably in the region of from about 2 mm to about 5 mm.

Where the band is applied directly to the outer surface of a ceramic cup, the ceramic will generally be shaped in the region of the rim where the band is applied such that when the band is in position, the external profile of the prosthesis (ignoring any ribs or other biting configurations) will correspond to that of a ceramic cup prosthesis not having a band. Thus the cup with the band will still have the approximately hemispherical outer configuration.

It will therefore by understood that the thickness of the band will generally be of the order of a few millimeters. The surface of the band which will be in contact with the cup will generally be flat whereas the outer surface of the band may be curved and as such the shape of the band in cross-section may be D-shaped. At the thickest point it may have a thickness of the order of about 1 mm to about 3 mm.

The flanges may be of any suitable size. Their lengths will generally be sufficient to enable them to connect to the impaction size. They may extend around the entire rim of the cup, or may be strips, or crenellations extending therefrom.

The band may be applied to the acetabular cup by any suitable means. In one arrangement, it may be press fitted onto the cup. Since the band is a tight fit on the cup, press fitting onto the cup may present difficulties. In one arrangement, the band may be heated to allow it to be correctly fitted. In one arrangement, the heating may be by induction heating. A benefit of induction heating is that only the metal band will be affected and the ceramic cup will not be heated. The induction heating may be carried out by any suitable means. The press fit may require load to be applied. The load required may depend on the temperature to which the band is heated. In one arrangement, heating may be to from about 500 to about 700° C. In one arrangement approximately 5 kN load may be used for the press-fitting.

Once the band has cooled, the loading of the band on the cup will generally act to pre-stress the cup in an optimum manner such that separation between the band and the cup will not occur. In this connection it will be understood that the band being metal is strong in hoop tension whereas the ceramic cup is strong in hoop compression. With the pre-stressing of the present invention, the tensions are optimised. In particular, the residual stress in the ceramic may be engineered to a value that optimises performance and is compressive. In addition, the compressive interface between the two components is maintained throughout the entirety of the loading of the prosthesis in vivo.

A further advantage of the acetabular cup prosthesis having the band located on its outer surface adjacent the rim is that it has sufficient strength to withstand the forces applied during the insertion of the prosthesis into the acetabulum without damage, distortion or separation of the band from the cup. In particular, and surprisingly, the sphericity of the prosthesis is substantially maintained even though the diameter is reduced due to the localised compression at the rim of the cup.

The prosthesis of the present invention may be provided with an impaction cap. The impaction cap may be pre-assembled with the prosthesis as described in co-pending application EP 2008618 which is incorporated herein by reference. In one arrangement the impaction cup is configured such that the force applied to impact the prosthesis into the acetabulum is directed via the ceramic cup so that any shock passing through the metal band is minimised.

The flanges may be formed integrally with the band or may be separate thereto but connected thereto by any suitable means. For example a flange may extend from the impaction cap, behind the band, and then be connected to itself in the region of the cap, to the impaction cap or to a component attached to the impaction cap.

The flange may be frangible by any suitable means. In one arrangement it may have a notched region to promote breakage of the flange when a force is applied in a particular direction such as by rotation of the impaction cap. In another arrangement the flange may be thinner in the region where it is to break. Whatever arrangement is used, it is important that the flange has sufficient strength in the appropriate direction that it does not break during impaction of the prosthesis but that it will readily break when required usually by application of a force in a direction not used during impaction.

The flange will generally be configured such that the end remaining attached to the band after breakage does not have a sharp edge. In a preferred arrangement, the flange will be engineered such that the edge of the flange remaining after breakage is below the rim of the ceramic cup. This has the benefit that the risk of there being any sharp edges which could contact soft tissue is removed or at least minimised.

Any suitable number of flanges may be used. In some arrangements, three flanges will be used. In an alternative arrangement, a flange may extend substantially from the whole of the band or a substantial portion thereof.

BRIEF DESCRIPTION OF THE DRAWINGS

The present invention will now be described, by way of example, with reference to the accompanying drawings in which.

DETAILED DESCRIPTION OF THE INVENTION

Figure 1:
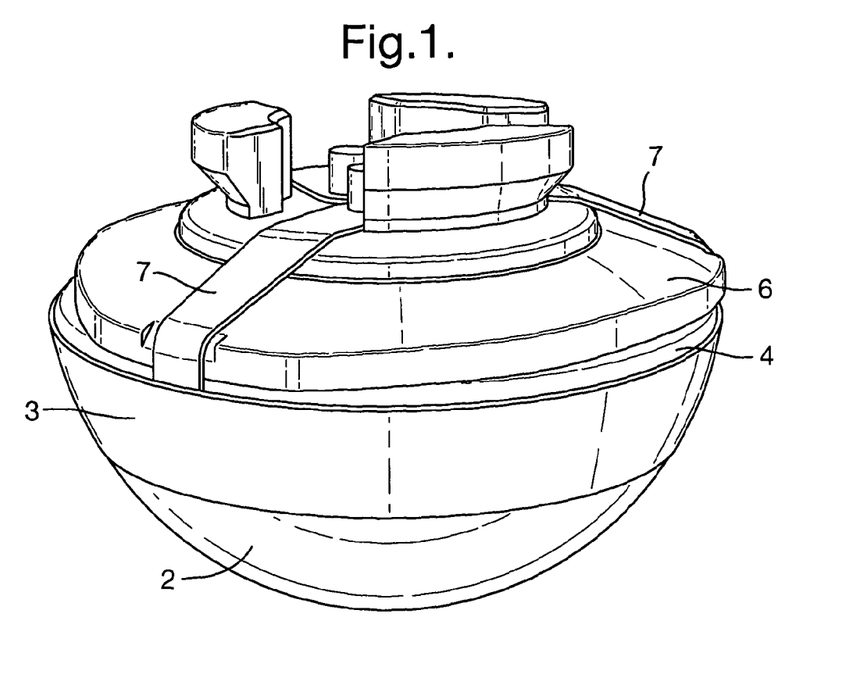
FIG. 1 is a perspective view of one example of the acetabular cup prosthesis of the present invention.
Figure 2:
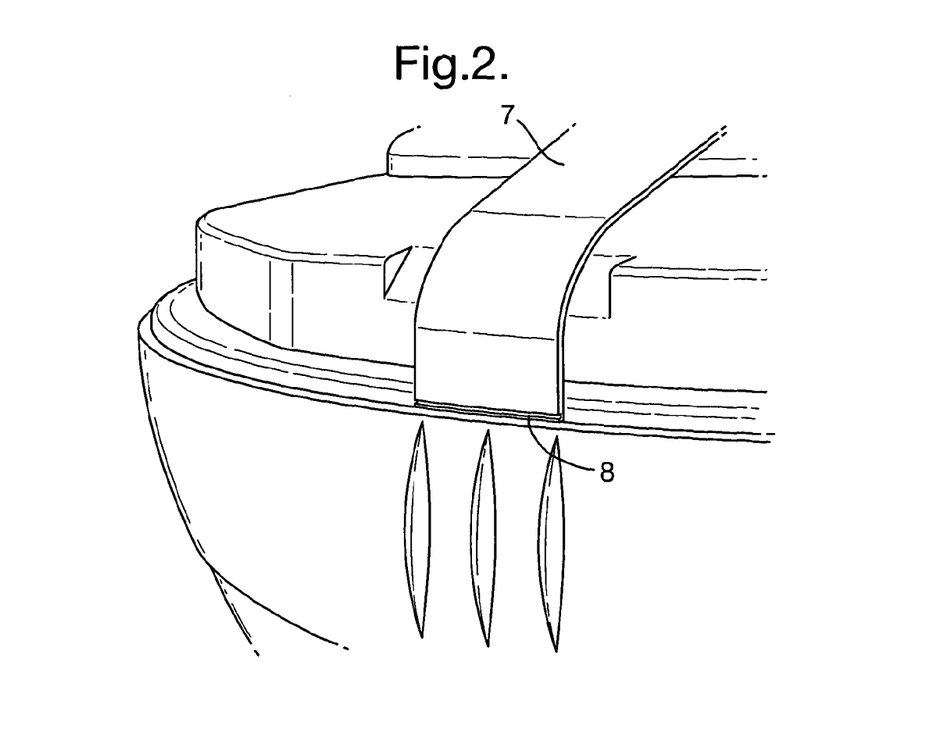
FIG. 2 is a close up region of a portion of the arrangement of FIG. 1.
Figure 3:
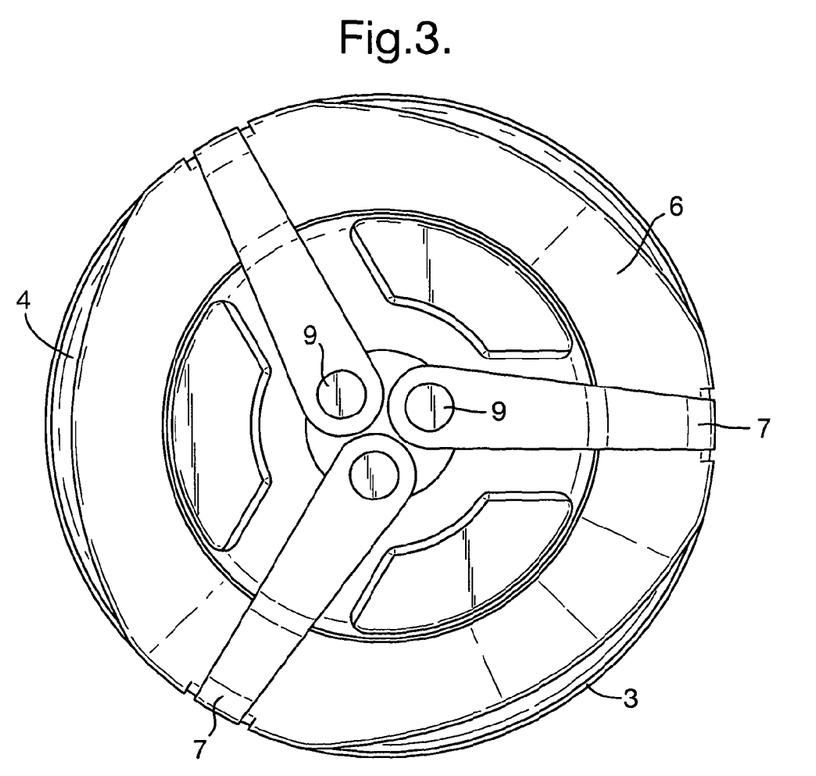
FIG. 3 is a view from above of the arrangement of FIG. 1.
Figure 5:
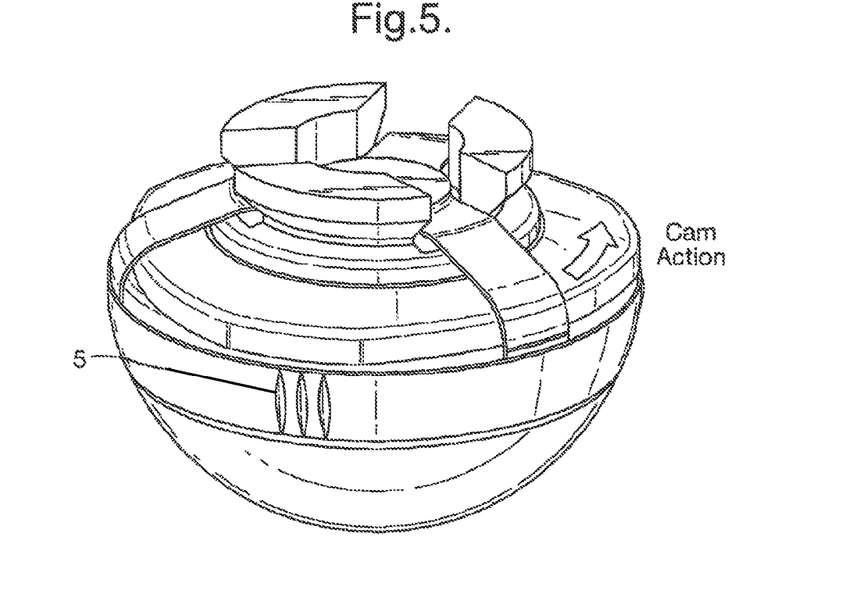
FIG. 5 is a perspective view of the arrangement of FIG. 4.

As illustrated in FIG. 1, the prosthesis 1 of the present invention comprises a cup 2 and a titanium band 3 located around the external surface of the cup and adjacent to the rim 4 of the cup 2. As illustrated in FIG. 5, ribs 5 are located on the external surface of the band and are configured such that when located in the pelvis torsional movement of the cup in the pelvis is resisted.

Figure 22:
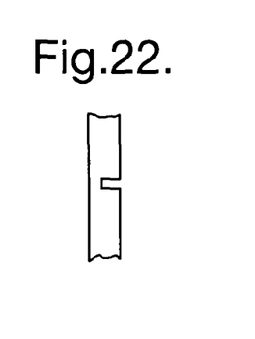
FIG. 22 is a schematic view of a portion of the flange.
Figure 23:
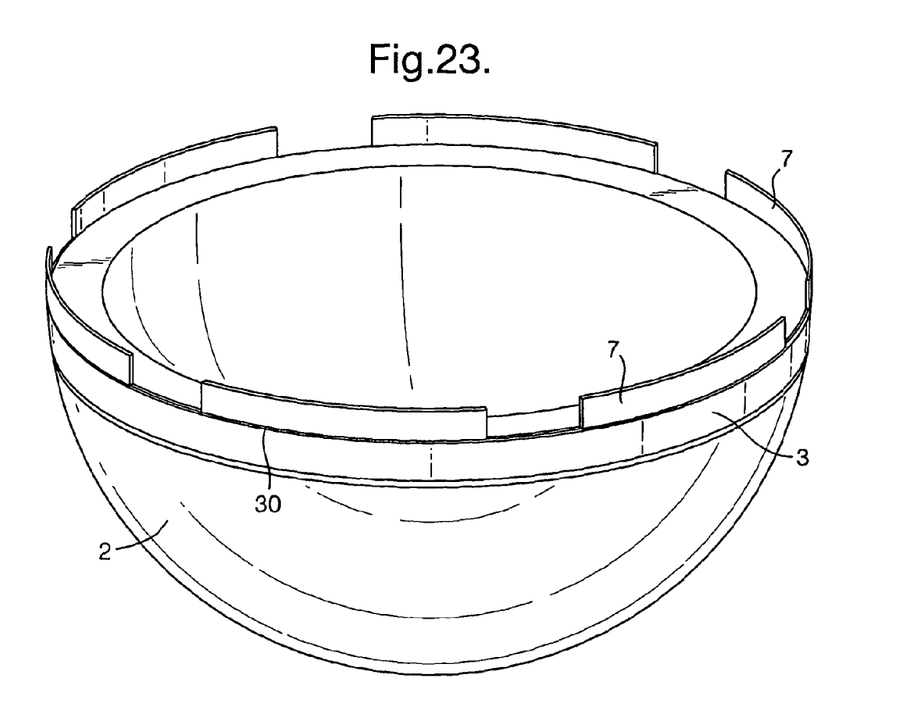
FIG. 23 is a perspective view of a still further arrangement.
Figure 24:
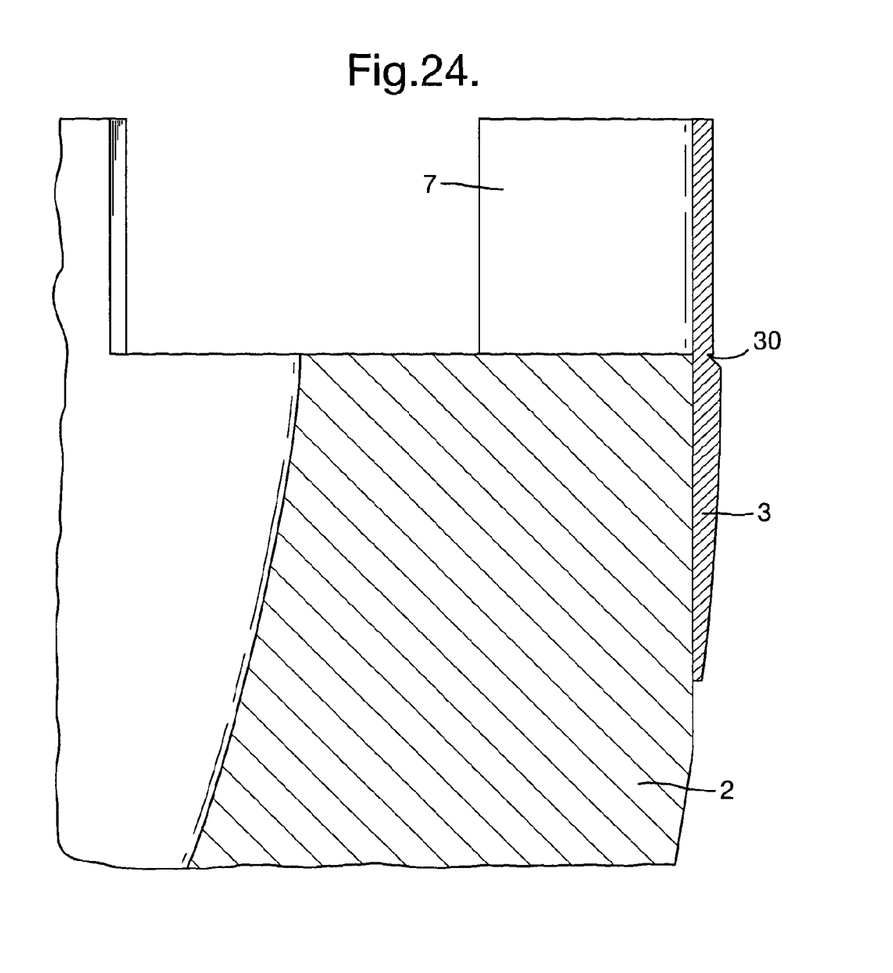
FIG. 24 is a partial side view of a portion of the cup of FIG. 23.
Figure 25:
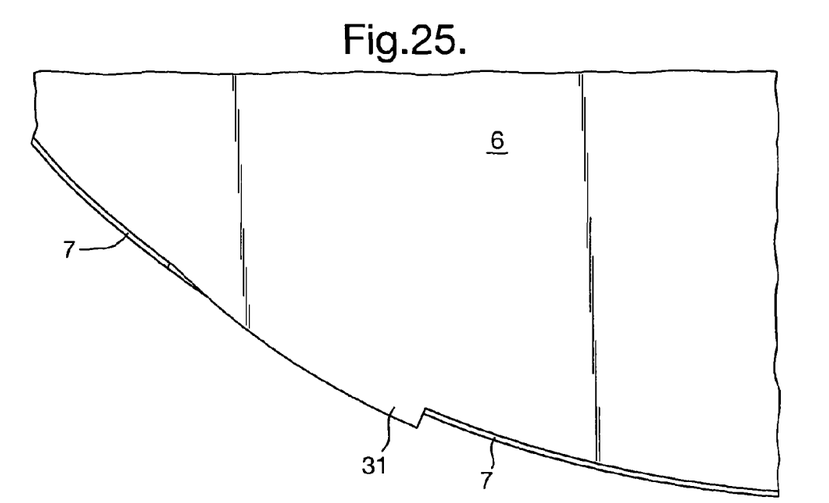
FIG. 25 is a partial side view of a profile of an impaction cap for use in the arrangement of FIG. 23.

An impaction cap 6 is connected to the prosthesis 1 by three flanges 7. Each flange 7 has a frangible region 8 a region which is thinner than the remainder of the flange 7 so that when required it can break. This is illustrated schematically in FIG. 22.

Figure 4:
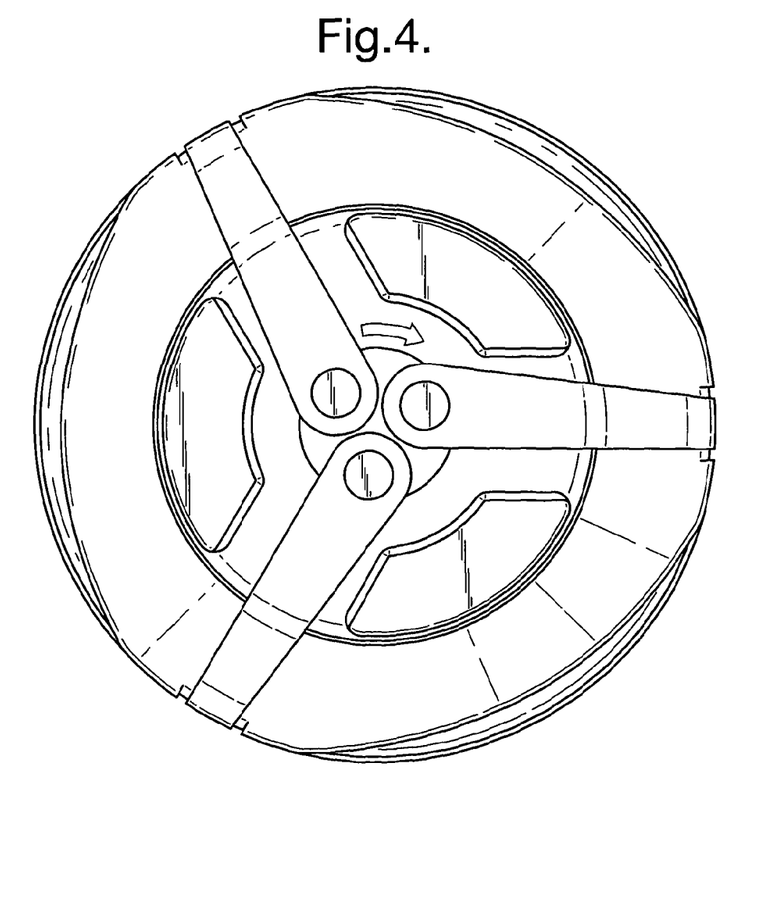
FIG. 4 is a schematic view of the arrangement of FIG. 3 showing the direction of the force required to cause the flanges to break.
Figure 6:
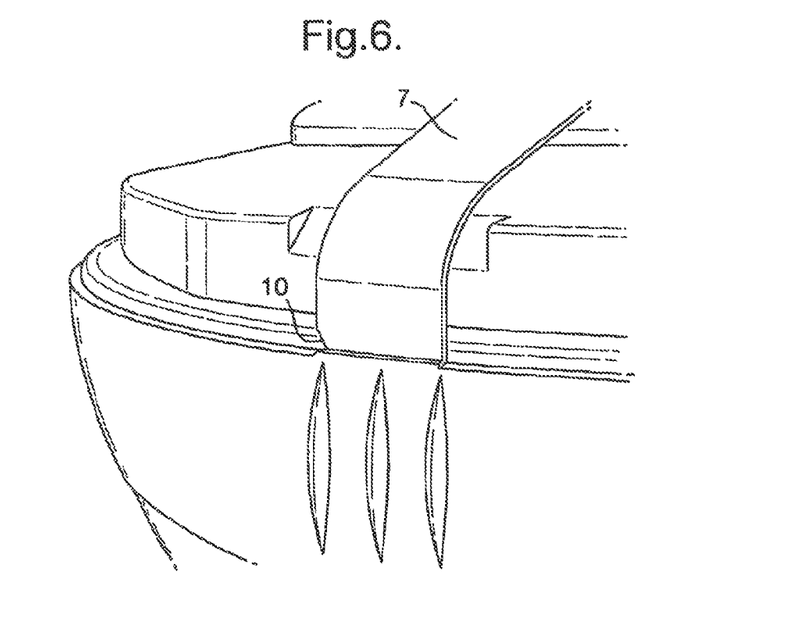
FIG. 6 is a close up view of a flange illustrating a notched arrangement.

The end of each flange 7 may be connected to a projection 9 on the impaction cap 6. Once the prosthesis has been inserted into the acetabulum of the pelvis, the cap 6 may be rotated in the direction of the arrow on FIGS. 4 and 5 to cause the flange to break. As shown in FIG. 6 a notch 10 may be provided to facilitate the breakage of the flange.

Figure 7:
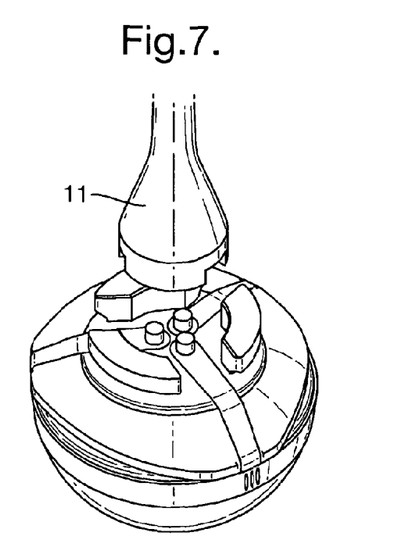
FIG. 7 is a perspective view from above of the arrangement of FIG. 1 illustrating a removal tool.

As shown in FIG. 7 a tool 11 may be used which will interact with the projections on the impaction cap to cause the rotation.

Figure 8:
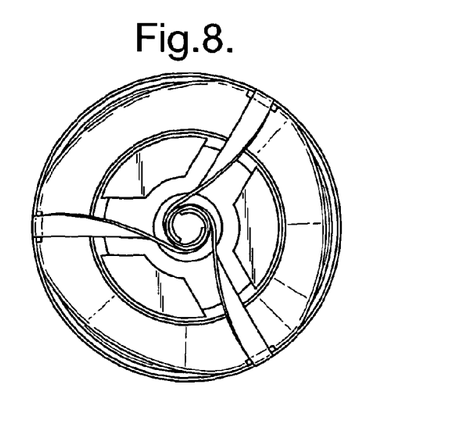
FIG. 8 is a view from above of an alternative arrangement of the present invention.
Figure 9:
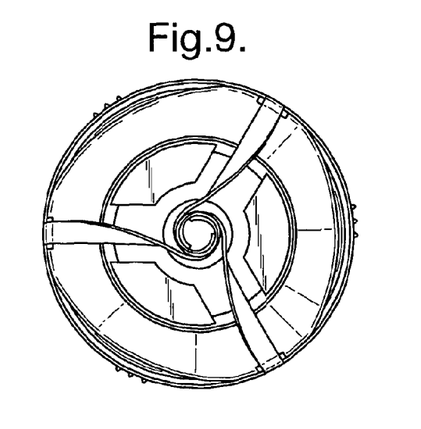
FIG. 9 is a further view of the arrangement in FIG. 8.
Figure 10:
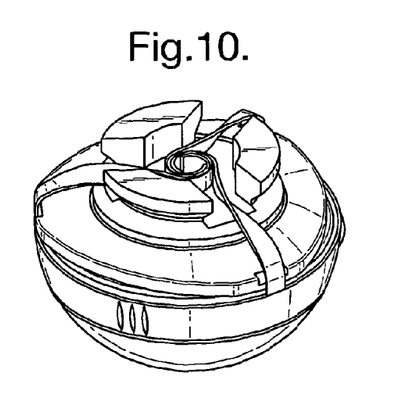
FIG. 10 is a perspective view of the arrangement of FIG. 8.
Figure 11:
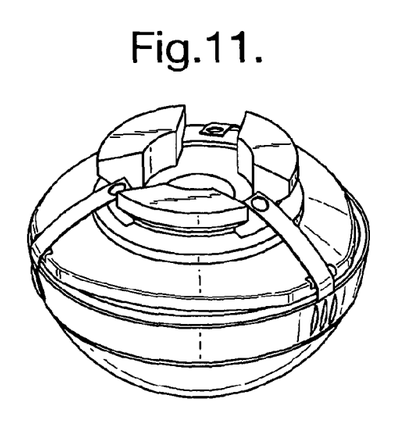
FIG. 11 illustrates a further embodiment of the present invention.
Figure 12:
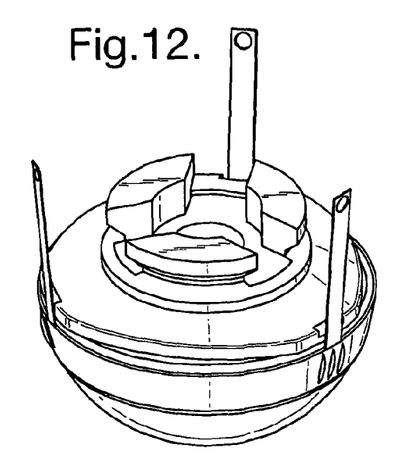
FIG. 12 illustrates the arrangement of FIG. 11 before the flanges are connected to the impaction cap.
Figure 13:
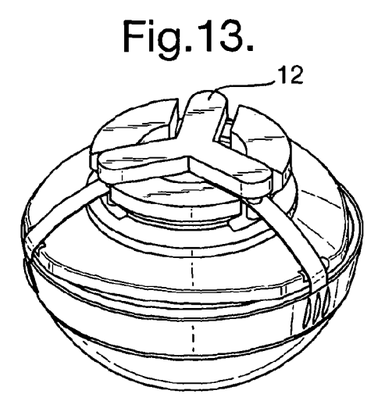
FIG. 13 illustrates the arrangement of FIG. 11 with the flanges connected tot he impaction cap.
Figure 14:
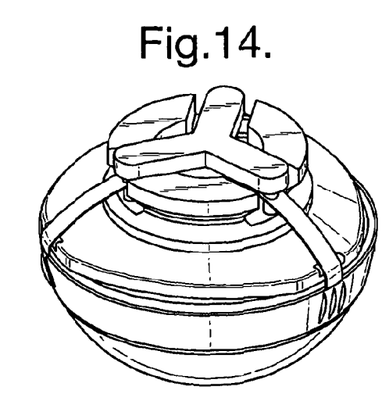
FIG. 14 illustrates a further view of the arrangement of FIG. 13.
Figure 15:
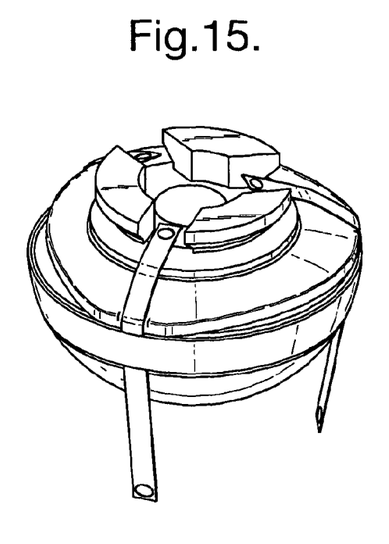
FIG. 15 is a perspective view of a still further arrangement of the present invention as the flanges are connected.
Figure 16:
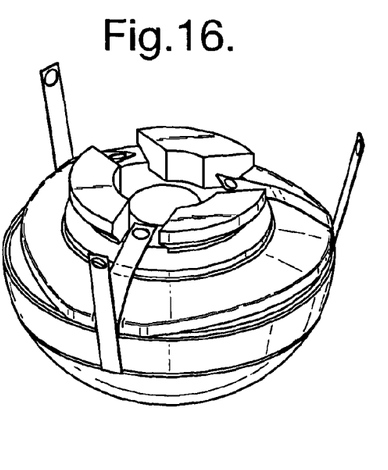
FIG. 16 is a further view of the arrangement if FIG. 15 as the flanges are wrapped around the band.
Figure 17:
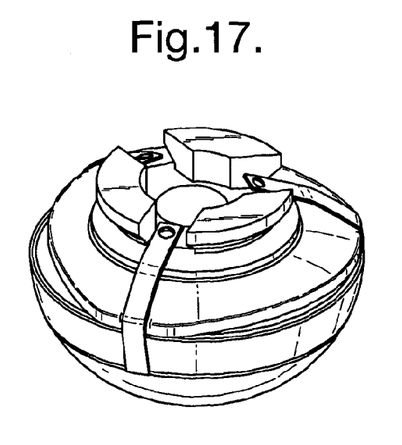
FIG. 17 illustrates the flanges connected to the impaction cap.
Figure 18:
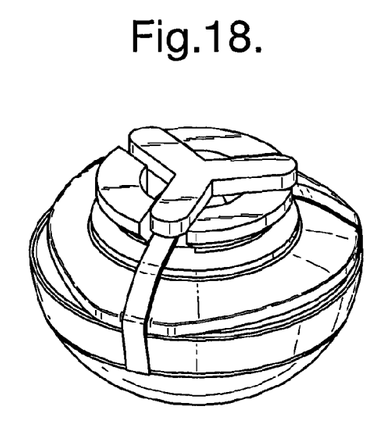
FIG. 18 is a perspective view of the arrangement of FIG. 15 with a connector in position.

The flanges illustrated in FIGS. 1 to 7 lay flat on the surface of the impaction cup. However, as illustrated in FIGS. 8 to 10 they may be twisted and attached to the centre of the impaction cap in a manner which will increase the ability of the flange to break when subjected to rotation.

An alternative arrangement is described in FIGS. 11 to 14 where the flanges are not attached to the centre of the impaction cap but to projections spaced toward the rim thereof. In this arrangement a connector 12 may be used to hold the flanges on the projections and to enable interaction with the tool which will cause the rotation to break the flanges.

In the arrangement of FIGS. 15 to 18 the flanges do not extend from the band. In contrast, the flange extends from the centre of the impaction cap, where they may be attached to the projections, outwardly, behind the band and then wrapped around the outer surface of the band before being connected to the projections. The respective ends of the flange may be connected to the same projection or to different projections.

Figure 19:
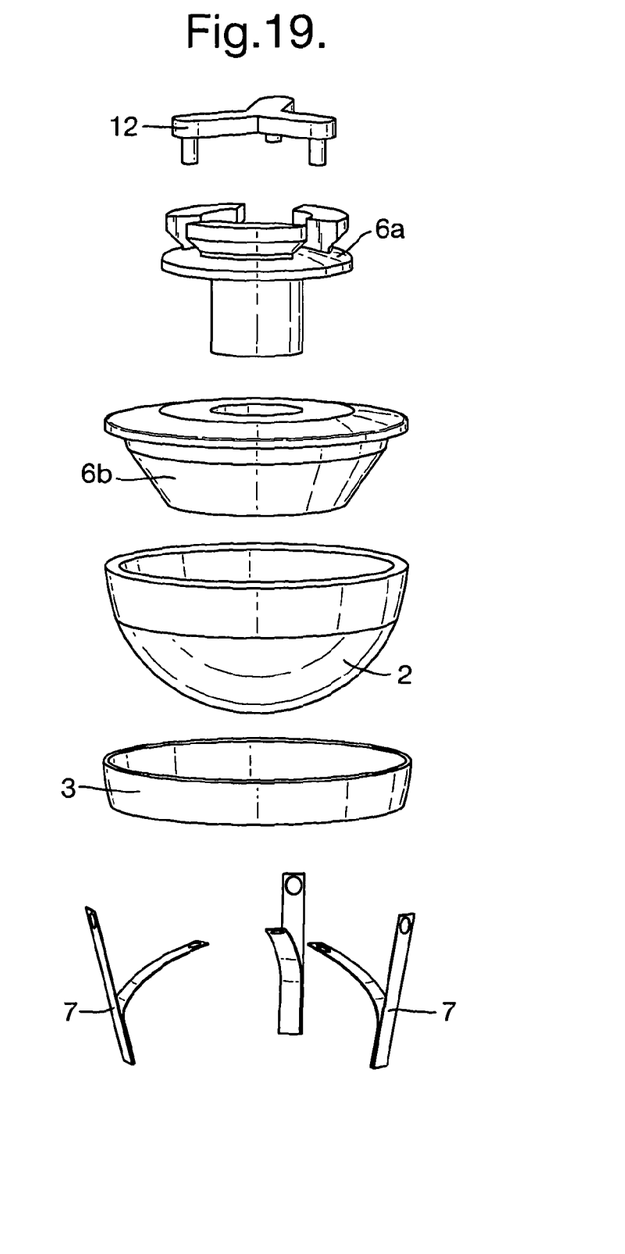
FIG. 19 is a schematic view of the components of the arrangement in FIG. 15.
Figure 20:
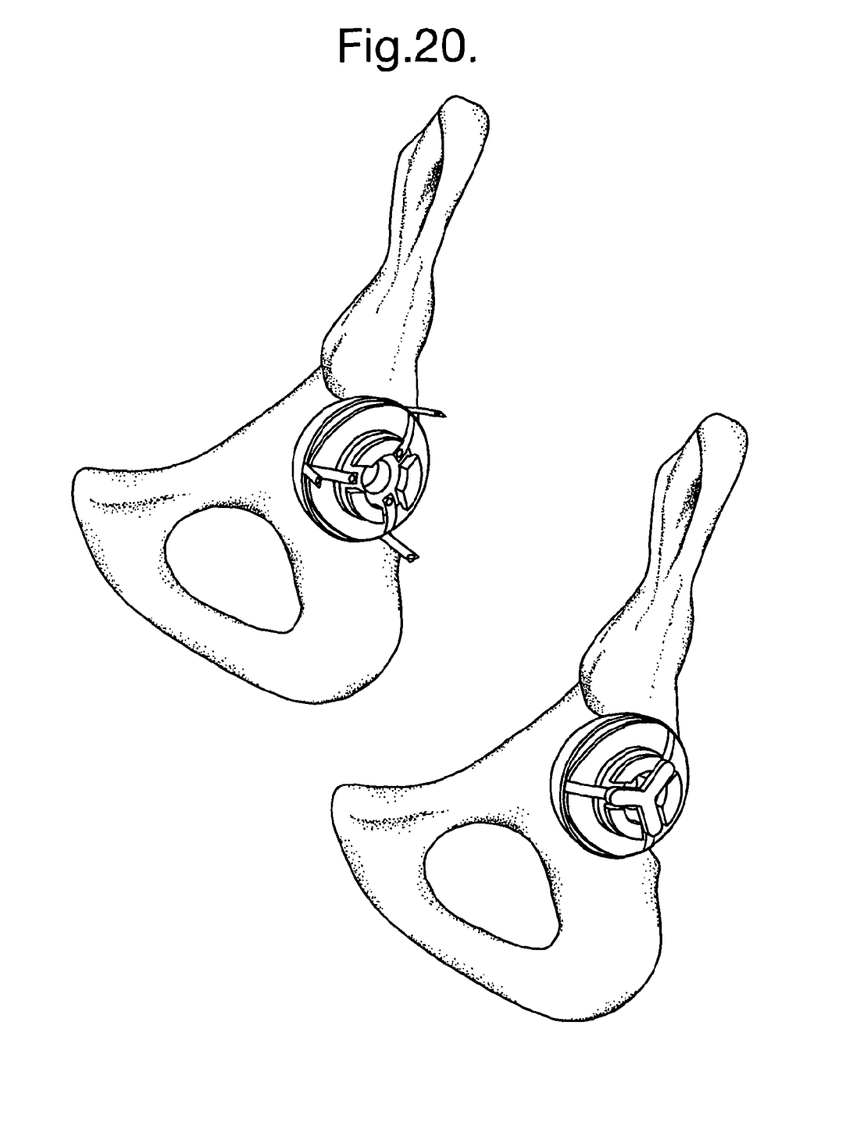
FIG. 20 illustrates the acetabular cup in position in the hip.
Figure 21:
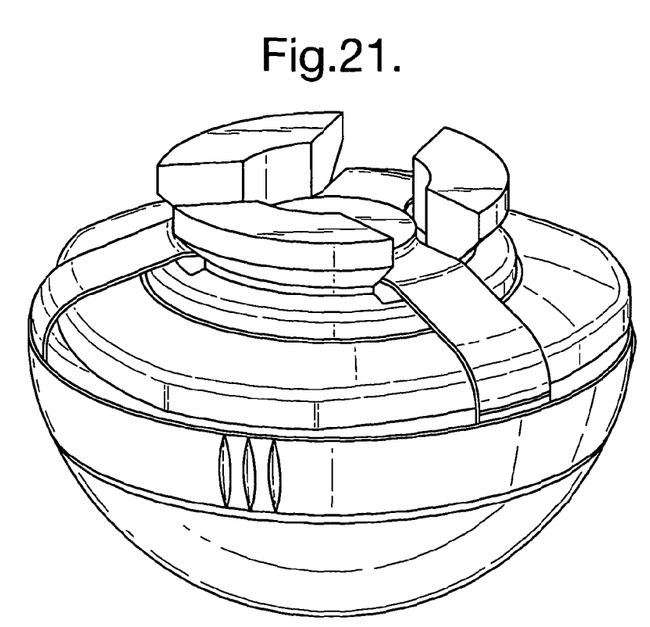
FIG. 21 is a perspective view of an acetabular cup prosthesis of the present invention.

As illustrated in FIG. 19, a complete arrangement may be formed from an acetabular cup 2, a band, flanges 7, an impaction plate formed of two components 6a and 6b, and a connector 12.

Whilst the present invention has been discussed in connection with an acetabular cup prosthesis comprising a cup and a band, it will be understood that the flange arrangement may equally be used in combination with a conventional acetabular hip prosthesis.

Figure 26:
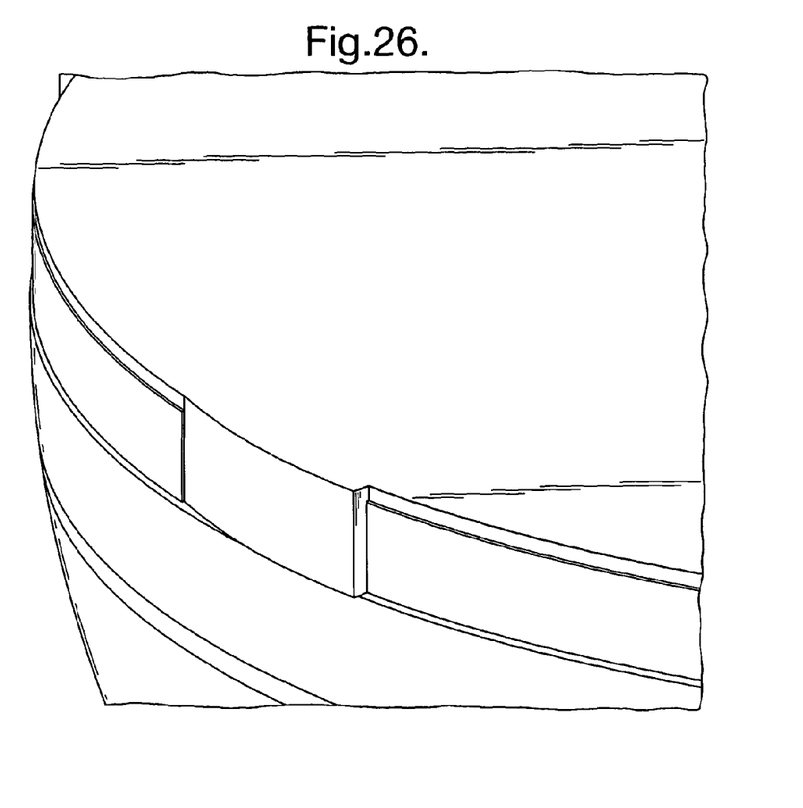
FIG. 26 is a partial perspective view of the impaction cap in position on the cup of FIG. 23.
Figure 27:
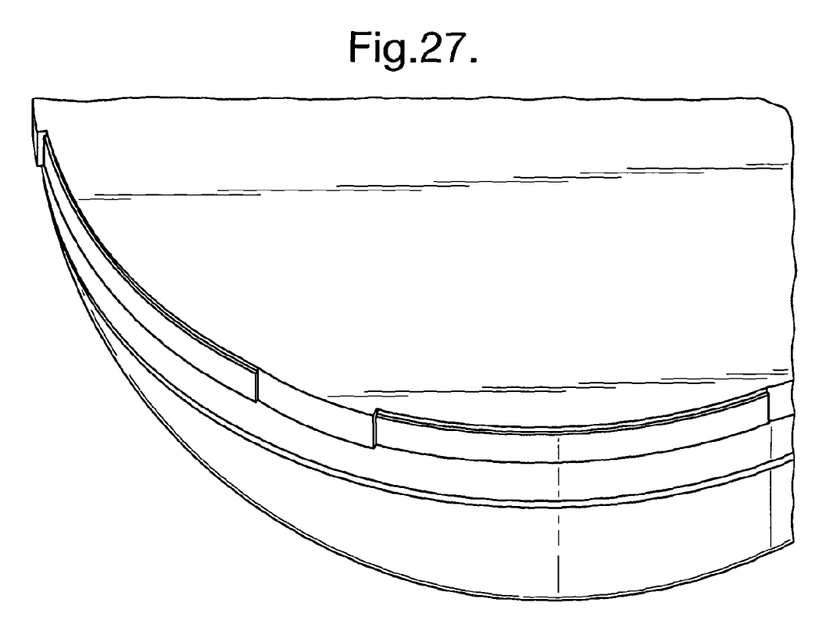
FIG. 27 is a further view of the arrangement of FIG. 26.

An alternative arrangement is illustrated in FIGS. 23 to 27. In this arrangement a flange 7 extends upwardly from the band 3. In general the flange may extend substantially around the entire circumference although there will be regions where the flange is not present to allow interaction with the impaction cap. The flange may be of any arrangement above the centre of the band 3. A thinner region 30 will be provided to enable the flange to be broken when required. This is illustrated in the partial cross-section of FIG. 24. In this embodiment the impaction cap 6 may be shaped to have lugs 31 which when in position in the cup extend through the regions where the flange is not present as illustrated in FIGS. 26 and 27. In this arrangement rotation of the impaction cap will cause the lugs to apply pressure to the flange to cause it to break.

The invention claimed is:

1. A cup prosthesis, the cup prosthesis comprising:
   a cup having an inner surface, a rim, a space defined by the inner surface and the rim, and an outer circumference;
   a band having an outer surface, the band being disposed about the outer circumference and adjacent to the rim;
   an impaction cap disposed at least partially within the space defined by the inner surface and the rim; and
   at least one flange extending from the band, the at least one flange having a second end, the second end being connected to the impaction cap; wherein a portion of the at least one flange is frangible.

2. The cup prosthesis of claim 1, wherein the cup is formed of a ceramic material.

3. The cup prosthesis of claim 2, wherein the band is configured to pre-stress the cup.

4. The cup prosthesis of claim 1, wherein the band is made from metal.

5. The cup of claim 1, wherein the at least one flange is made from metal.

6. The cup prosthesis of claim 1, wherein the band has a band circumference, and at least one rib that extends away from the outer surface.

7. The cup prosthesis of claim 6, wherein the at least one rib comprises at least two ribs, each of the at least two ribs being located at spaced apart locations on the band.

8. The cup prosthesis of claim 6, wherein at least one of the at least one ribs extends longitudinally from the outer surface of the band.

9. The cup prosthesis of claim 6, wherein at least one of the at least one ribs extends longitudinally from the outer surface of the band perpendicular to the the band circumference.

10. The cup prosthesis of claim 1, wherein at least a portion of the outer surface of the band is coated with a bone growth promoting material.

11. The cup prosthesis of claim 1, wherein the cup is an acetabular cup.

12. The cup prosthesis of claim 1, wherein the impaction cap has an outer surface and at least one projection extending from the outer surface, and the second end of the at least one flange is connected to the at least one projection.

13. The cup prosthesis of claim 12, wherein the second end has an opening sized to accept the at least one projection.

14. The cup prosthesis of claim 13, wherein the at least one projection is circular in cross section and the opening is circular and sized to accept the at least one projection.

15. The cup prosthesis of claim 1, wherein the at least one flange comprises three flanges, and each of the three flanges are spaced apart one from the other about the circumference.

16. The cup prosthesis of claim 15, wherein the impaction cap has an outer surface, a center axis, and three projections extending from the outer surface, the three projections being spaced apart one from the other radially about the center axis.

17. The cup prosthesis of claim 1, wherein the frangible portion is thinner than an adjacent portion of the flange.

18. The cup prosthesis of claim 1, wherein the frangible portion is located proximate the band.

19. The cup prosthesis of claim 1, wherein the frangible portion is located below the rim of the cup.

* * * * *